United States Patent [19]

von Nostitz

[11] Patent Number: 4,759,798

[45] Date of Patent: Jul. 26, 1988

[54] PROCESS FOR THE PREPARATION OF DENTAL-TECHNICAL, DENTAL-MEDICAL AND MEDICAL MOLDING AND LINING MATERIALS

[76] Inventor: Frauke H. F. von Nostitz, Widenmayerstr. 17, D-8000 Munich 22, Fed. Rep. of Germany

[21] Appl. No.: 819,160

[22] Filed: Jan. 14, 1986

[51] Int. Cl.$^4$ .............................................. C09K 3/00
[52] U.S. Cl. ...................................... 106/35; 523/115; 523/116; 523/117; 523/109; 260/998.11
[58] Field of Search ................. 106/35; 523/115–117, 523/109; 260/998.11

[56] References Cited

U.S. PATENT DOCUMENTS 3,620,778 12/1971 Morrell ............................... 528/950
4,366,099 12/1982 Gaetani et al. ..................... 525/279
4,438,140 3/1984 Guillon et al. ..................... 525/153
4,497,919 2/1982 Varga et al. ........................ 524/42

*Primary Examiner*—Morton Foelak
*Assistant Examiner*—M. L. Moore
*Attorney, Agent, or Firm*—Wolf, Greenfield & Sacks

[57] ABSTRACT

A process for the preparation of dental-technical, dental-medical and medical molding and lining materials including the steps of mixing a substrate selected from the group consisting of a monomeric and/or polymeric or copolymer acrylic or methacrylic ester, a hardening substance for the substrate. Wherein jojoba oil in present in an amount of 0.05 to 10% of total material and the substrate is present in amount of at least about 60% if the total weight of the material.

19 Claims, No Drawings

PROCESS FOR THE PREPARATION OF DENTAL-TECHNICAL, DENTAL-MEDICAL AND MEDICAL MOLDING AND LINING MATERIALS

The invention concerns a process for the preparation of dental-technical, dental-medical and medical molding and lining materials.

The use of acrylic or methacrylic acid esters for the manufacture of dental-technical and dental-medical molds, especially when taking jaw impressions as well as for the inner lining of plastic dentures etc., is known. It is also known that additives such as plastics of another type, cellulose derivates, (natural) resins (e.g. copal, sandarac), paraffin, wax, oil, dyes and fillers should be added for this purpose to the acrylic substances for dental-technical and dental-medical purposes.

The acrylic or methacrylic acid ester is generally used in such a way that a powder, bead or splinter granulate of a polymer or mix polymer of these compounds is dissolved in a liquid monomer and this solution is hardened optionally with addition of promoters. But when using such mixtures there are certain drawbacks.

While the dissolution of the powder in the liquid is relatively time-consuming, in the case of cold polymerization in the powder-liquid system, parts of the polymer remain undissolved, which causes a loss of stability and homogeneity of the material. It is desirable to provide a process whereby a material is obtained which ensures easier workability, optionally on the basis of improved viscosity and plasticity of said material.

The cold polymers containing monomeric methylmethacrylate are also regarded as irritating to mucous membranes. In this respect too it is desirable to create an improved process which would avoid or reduce this disadvantage. In addition burns can result in the mouth from the rapid polymerization of cold polymers. When producing dental linings from monomeric methylmethacrylate, the products do not always have perfectly smooth surfaces, and are therefore partially absorbent of the saliva; this, however, is disadvantageous as to growth of microflora in the mouth.

The invention is therefore based on the object of providing a process of the type above whereby a molding and lining material with an improved viscosity is obtained, which ensures easier and faster processing, has better mechanical strength and develops a healing effect at pressure points and points of inflammations, forms smooth surfaces, is devoid of smell and taste as well as being compatible with the mucous membranes, while maintaining optimal fitting over more lengthy periods of time. Besides, the material obtained by the process according to the invention should be easily adjustable if necessary to the required consistency, e.g. hard or elastic or remaining soft, respectively.

The object above is solved according to the invention by providing a process of the type above which is characterized in that it comprises the mixing of a monomeric and/or polymeric or copoylmeric acrylic or methacrylic ester, a hardening substance for respective acrylic or methacrylic ester and 0.05 to 10% by weight of jojoba oil.

The above jojoba oil as used in the invention is the oil of the jojoba plant, which belongs to the buxaceae family, after extraction and purification. Hereinafter the term jojoba oil, as used in the invention, also covers jojoba wax.

It is preferable to use the jojoba oil together with the other components for the manufacture of dental-technical, dental-medical and medical molding and lining materials according to the invention in a concentration of 0.1 to 5% by weight.

Jojoba oil, butter or wax may be considered as an ecologically beneficial substance. It is assumed that by mixing jojoba oil with acrylic ester, the jojoba oil adheres rather strongly to the ester molecules, whereby the disadvantageous properties of the latter are eliminated. This is of special interest in view of the negative effect caused by remaining monomeric units of acrylate. It seems that jojoba oil covers the acrylic monomer with a thin film, thereby reducing its reactivity which may be detrimental when used as a mold or lining. This positive effect due to the addition of jojoba oil or wax is especially valuable in cold polymerizations. Thus, the addition of jojoba oil to the acrylic acid mixture enhances greatly the compatibility of the latter.

By adding jojoba oil to the molding and lining material as in the invention, it is possible to improve the workability, toughness, hardness and strength as well as the surface properties and the durability of the dental-technical, dental-medical and medical molds made therefrom (no aging manifestations), as well as the brittleness, odor formation, and unattractive color formation; further, said material develops a healing effect at the pressure points, e.g. in the oral region, as well as with linked dentures. By the addition of jojoba oil according to the invention a non-porous, non-brittle and non-shrinking material is obtained, which is also especially compatible with the mucous membranes and which is suitable for the most varied dental-medical, dental-technical and medical purposes to an outstanding degree. Using said material it is in particular possible to attain elastic, hard or permanently soft molds or inner linings as desired, in which the hardness or the elasticity can be regulated fully as required. In particular, said molding material obtained by the inventive process is characterized by the fact that optionally plastic or hard dental-technical, dental-medical or medical molds can be produced which maintain their optimal fitting and viscosity or plasticity over long periods, develop a healing effect at sore points and possess a good mucous membran compatibility.

As the solvent or dispersing agent for the homo- or mix-polymer share, the methyl ester of acrylic and/or methacrylic acid can be used. Hot polymerization of acrylates can also be carried out without the methyl ester additive. This embodiment of the invention is considered especially when hot polymerization is effected or when for dental purposes the polymerization in the mouth of the patient himself is omitted. An especially preferred substance according to the invention has however no substantial share or no share of monomeric acrylic acid or methacrylic acid methyl esters, but instead of them high boiling point ester derivates of the named acids are used. Here special consideration is given to a content of at least one monomeric acrylic and/or methacrylic acid ester having from 6 to 10 carbon atoms. Examples are provided by 2,3-epoxypropyl-, n- or t-butyl, n- or cyclohexyl-methacrylic acid ester or mixtures of these monomers. Equally good use can be made of the analogous esters of the acrylic acid, while it may be especiall expedient to use mixtures of the named monomeric acrylic acid esters and methacrylic acid esters. Although the use of ester derivates with a total of from 6 to 10 carbon atoms is preferred, at least partially ester derivates of acrylic or methacrylic acid may be used, whose total carbon number is below the range shown as preferred above from 6 to 10 carbon atoms, for example methacrylic acid-dodecyl ester, methacrylic acid-triethylenglycol-mono-ethyl ester, methacryl acid-ethylhexyl ester etc. A specially advantageous monomer is lastly a reaction product of glycidylmethacrylate and bisphenol A.

The polymers may be basically polyacrylates and -methacrylates or mix and or copolymers. In addition certain shares of plastics of another type may be present, such as polyvinylchloride, polyvinylacetate, or polyvinylalcohol. Preferred is a mixture of polymethacrylates with average molecular weight. Among them especially favorable are those which have good solubility properties in the monomeric shares used and in the solvent shares partly contained therein. Such polymethyl methacrylate mixtures of average molecular weight, which for example are soluble in esters, ketones, chlorinated aliphatic hydroarbons, cyclic ethers, etc., and have thermoplastic properties, can be obtained from the trade.

Preferably the acrylic and/or methacrylic esters used in the inventive process represent a mixture of monomers and polymers or of mix polymers of acrylic and methacrylic acid esters. This mixtures is preferably present as a paste or as a solution.

The polymer share in the monomeric solution, which optionally contains additives, can vary within wide limits. Normally polymer shares between 10 and 70% by weight based on the total composition are present. A specially preferred range of the share of the polymer amounts to from 10 to 40% based on the total substance, since it easily provides especially fluid-to-pasty and doughy mixtures which can be cast, injected, distributed with the spatula or squeezed as fluid, doughy or pasty materials from pressure vessels and thus distributed.

To these solutions or syrup, pastes or doughy mixtures of polymers or mix polymers in the monomer, metal soaps and/or silicates, a hardening substance (catalyst) and optionally an accelerator are added for hardening.

Stearates, laurates, oxystearates, palmitates, montanates, oleates or ricinoleates of metals such as for example aluminium, magnesium, or calcium have been found suitable as the metal soaps. Preferred are the alkaline earth soaps, which should be present in finely divided form. Special preference is given to the use of magnesium stearate and calcium stearate. The added amount of metal soap(s) adds up advantageously to from 0.1 to 10% by weight, based on the total substance.

As the silicates whose addition has been found favorable it is primarily alkali silicates which are considered, especially the trade-obtained soluble waterglass compounds of which both sodium- and calcium silicate or mixed alkali silicates can be used. Especially suitable is alkali aluminium silicate. The amount added of such a silicate is preferably 1.5% to 5% based on the total amount of the substance. In these waterglass preparations, the so-called oil number should not be more than 26, while an oil number of about 22 has performed especially well.

In the event of special stress on the molding and lining material for dental-technical or dental-medical and medical uses, it may be expedient to provide a share of a cross-linking agent. Among the known substances effective for the cross-linking of methacrylate or acrylate, special suitability attaches to olefinic dimethylacrylates such as ethylene dimethylacrylate, propylene dimethylacrylate, polyethyleneglycol dimethacrylate. It is expedient that the optionally used polyethyleneglycol dimethylacrylate cross-linking agent should have a relatively low molecular weight. The cross-linking agent which is especially suitable for the prevention of the later emergence of stress cracks can for example be added in amounts of from 0.1 to 10% by weight, based on the total substance.

The cross-linking agent can however also be used in larger amounts and can partly replace the monomeric (meth)acrylate. According to one embodiment of this invention, which can be seen as being preferred for certain applications, the monomeric share is totally replaced by a monomeric cross-linking agent. In the latter case, the polymer share would be exclusively dissolved in the monomeric cross-linking agent.

In one preferred embodiment the inventive process for the manufacture of plastic or hard materials for dental-technical and dental-medical and medical purposes makes use of a two-component system, with special preference for a powder system and a liquid system in which the powder system includes the polymeric acrylic or methacrylic ester and optionally the metal soap, a filler and a hardening substance (catalyst, preferably a peroxide), while the liquid system includes the monomeric acrylate or methacrylate, the softener, the accelerator as well as the jojoba oil.

Moreover to increase the storage time of the acrylic or methacrylic composition, a small amount of stabilizers or inhibitors is added thereto, which prevents any unintended further polymerization of the solution when it is stored. For this purpose, e.g. the phenol compounds such as aminophenol, dibutylmethyl-phenol, or butylhydroxyanisol or even hydroquinone, pyrogallol, or pyrocatechol may be considered. These inhibitors can be added in amounts of from about 2 to 100 ppm of the substance.

Methacrylates usually have a typical bitter aftertaste, which temporarily, for example when fitting the (functional) impression tray with the molding material or the lining of the denture, may be found disturbing. To overcome this problem, the addition of sweeteners free of carbohydrates, such as cyclamates, or of anti-cariogenic sugar additives on a carbohydrate base, for example xylite, to the molding and lining material may be performed; the mixture of sodium cyclamate with 10% saccharine well known in the trade has been found specially useful. Moreover the solution can contain the usual colorants.

The catalyst or hardening substance used to harden the acrylic or methacrylic esters may be added basically in powder form. But it is used with advantage in the form of a solution since in this way it is distributed easily and evenly in the acrylate solution. In the manner known per se, for the hardening substances one can use peroxides, such as hydrogen peroxide, tert.-butylhydroperoxide, cumylhydroperoxide, as well as dialkyl- and diarylperoxides, ketone peroxides, diacylperoxides such as di-benzoyl peroxide, or peroxide acids, as well as azo compounds, such as azo-di-isobutyric acid nitrile and azodicarbonamide, which are used optionally in solvents such as dibutyl-phthalate, methanol, acetic ester, acetone or methylethylketone.

In the case of catalyst systems which are self-hardening, i.e. the hardening is effected without the additional use of heat, an accelerator or activator, which effects the decomposition of the hardening substance and thus the start of the polymerization of the monomer into polymer, should be included. For such acceleration, tertiary amines, alkyl-, alkylaryl- and oxyalkylamines have proved satisfactory, as well as reducing agents such as sulphinic acids or dithionite, which can be added in amounts of from 1 to 3% by weight. But instead of the above listed catalyst systems, naturally all the other systems usable for the polymerization of acrylates or methacrylates may be employed. For example as the accelerator, consideration may be given to paratoluene amine in amounts of between 0.5 and 2% by weight.

But the hardening can also be performed in the absence of accelerators, for example by the influence of ultraviolet rays. In the case of hot polymerization the hardening is achieved without an accelerator by the supply of heat.

The inventive process is preferably carried out in such a way that directly before the preparation of the molding and lining material, a two-component system which consists of a powder system comprising the polymer, and optionally fillers and metal soaps, and a liquid system consisting of the monomeric acrylate, wich optionally comprises a softener, accelerator, and jojoba oil, is mixed.

In the practical use of the molding and lining material obtained by the inventive process, for example for lining a prosthesis, the material is applied on the previously roughened surface of the prosthesis which has expediently been solvated with a solvent, then the prosthesis is inserted into the mouth of the patient, where within a few minues the substance fully polymerizes under pressure and optionally with the exclusion of air. When carrying out repairs to dental prostheses, for example, it is advantageous to cover the applied molding or lining material with glass- or cellophane paper, since the hardening should take place expediently with the exclusion of air.

Using the molding and lining material obtained by the inventive process for dental-medical, dental-technical or medical purposes has the great advantage that now only the finished polyacrylate solution has to be made to solidify in the minimal time by adding a catalyst solution, preferably in the form of a two-component system comprising a powder system and a liquid system, without any shrinkage or aging of the material taking place with the passage of time, while the optimal fitting and molding can be attained. As seems desirable, elastic, permanently soft or hard molding or lining substances can be obtained and the polymerization can take place e.g. entirely in the mouth of the patient, without burns, erosions or irritations of the mucous membranes occuring, even in the case of cold polymerization.

The above molding and lining materials are primarily suitable for dental purposes, such as the individual production of an adapted (functional) impression tray with the corresponding molds for the manufacture of a dental prosthesis, as the molding and lining material for the production of a tooth guard, expecially for sportsmen, as is described in U.S. patent application Ser. No. 541,318 from the applicant which was filed on Oct. 13, 1983, and generally as impression substances, for linings and repairs of dental prostheses. In this connection it is of special interest that the carrier of the prosthesis can repair the same in self-medication by applying the lining or molding material obtained according to the inventive process.

In the medical field the above lining and molding material finds wide application, e.g.
for the manufacture of substitute parts of the body in the form of a hard or soft plastic,
for the production of soft portions and bone portions of the human body,
as a lining material for prostheses, e.g. leg and arm prostheses,
as a skin replacement material, e.g. after accidents and cancer operations,
for cosmetic corrections of the human body,
as finger nail replacements,
for the production of any type of medical valves, e.g. catheters, parts of drop-bottles,
for the production or repair of hearing aids,
for the manufacture of inner supports in shoes.

A special advantage of the molding and lining materials obtained by the improved process according to the invention consists of the fact that owing to their easy manipulation, they can also be used in self-medication, e.g. for those who use partial or total dental prostheses, for cosmetic corrections in self-medication, such as for example corrections of the laughing wrinkles for users of prostheses.

In the following there is given a listing of the properties of products obtained according to the inventive process with the addition of jojoba oil as compared to products containing no jojoba oil:

| Addition of jojoba oil | no addition of jojoba oil |
| --- | --- |
| A Surface Properties | |
| Velvet-like, homogeneous, non-porous surface; not irritating to mucous membranes. Jojoba oil forms a thin, non-distructable film between separate parts. | Partly rough surface; tendency to form surface cracks; partly porous. May be irritating to mucous membranes. |
| B | |
| Excellent fitting, possibility to adapt and repair a denture in self-medication by carrier of prosthetis himself; no express need of technical dental instruments for adjusting or repair of such dentures; no shrinkage on aging. | Reduced fitting after aging; no possibility of self-repair or self adjustment of dental prostheses. |
| C | |
| High flexibility, possibility of precise adjustment of desired degree of softness or hardness of lining or mold. Thus, no strangulation of blood circulation. Shore-A-hardness = 35 at mouth or body temperature; shore-A-hardness = 70 at roomtemperature. Above high flexibility of the material is due to the difference of hardness at varying temperatures. Thus, high thermoplasticity of the material. | Shore-A-hardness = 60 at mouth or body temperature; shore-A-hardness = 85 at room temperature (23° C.). Thus, lower flexibility, which my cause pressure on blood vessels at those parts of the body which prothesis. |
| Due to this high flexibility material shows at its surface properties similar to natural skin; it extends and shrinks like skin under the influence of temperature. | No skin-like behaviour. |
| D | |

| Addition of jojoba oil | no addition of jojoba oil |
| --- | --- |
| Low content of remaining monomeric acrylate: 1–2, 2% at 10 to 19% refinding (not reacted). Thus, high compatibility with surrounding tissue. | 4–5% at 45% refinding (not reacted). Reduced compatibility. |
| E Polymerization | |
| Lining and molding material may be polymerized solely with hardening substance, e.g. peroxide; no need to add accelerator, e.g. p-toluene amine. | Addition of hardening substance + accelerator obligatory. |

The following examples are to explain in more detail the inventive process, without limiting the scope of the invention. The named components in the examples may be present in the form of separate preliminary doses, optionally as a kit.

EXAMPLE 1

In a mixing vessel, 25% parts by weight of a copolymer consisting of 96 parts by weight of methyl methacrylate and 4 parts by weight of ethyl acrylate are mixed in 75 parts by weight of acrylic acid cyclohexylester, to which 1% p-toluene amine and 2% 1,4-butanediol-dimethacrylate are added. Instead of the cycloalkylester one can also use 65 parts by weight of a mixture of methacrylate tertiary butyl ester and methacrylic methyl ester in a ratio of 1:1 or 1:2. To the syrup thus obtained 2% of a normal trade alkali aluminium silicate and 2.5% of magnesium stearate as well as 1% of jojoba oil are added.

When using, a solution of 5 parts by weight benzoyl peroxide dissolved in 25 parts by weight of dibutylphthalate is added to this mixture dropwise. After a short time the substance begins to become viscous, so that it can now be applied to the prepared prosthesis and inserted in the patient's mouth. In a few minutes it hardens, forming a hard inner lining.

EXAMPLE 2

50 parts of a copolymer, comprising 96 parts by weight of methyl methacrylate and 4 parts by weight of ethyl acrylate, are dissolved in a mixture of 50 parts of methacrylic tertiary-butyl ester, methacrylic methylester and methacrylic n-hexylester, which are mixed in a ratio of 1:1:1. To this quantity 3% of magnesium stearate and 1% of a commercial alkali aluminium silicate, 1% p-toluene amine and 1% jojoba oil are added. As in example 1, to process this substance a benzoylperoxide solution is added dropwise and in a short time a viscous substance is obtained which is easy to spread on the prosthesis and quickly provides an elastic lining which has an excellent fit, is stable and shows almost no shrinkage.

EXAMPLE 3

A dental guard for sportsmen was prepared as follows, wherein the starting point was a functional impression tray such as is described in U.S. patent application Ser. No. 541,318. This impression tray of a thermoplastic material is adjusted to the individual dental and jaw situation by light pressure after immersion in hot water at 70° C. in order to soften it. Respective functional impression try is preferably prepared from the molding material obtained by the inventive process.

In the following a lining material consisting of 50% by weight of polyacrylate, about 55% by weight of metacrylic hexyl ester, 1% by weight of calciumstearate, 1% by weight jojoba oil, and an adequate amount of peroxide as hardener, is poured into the function impression tray, and the latter is again adapted to the dental and jaw conditions in the mouth. The above lining material was produced from a two-component system which was mixed directly before use. After about 10 minutes the elastic lining material had polymerized and formed a soft buffer zone between the relatively hard material of the tray and the teeth. To the extent that the impression tray used is provided with recesses in the occlusal overlay area, a part of the lining material penetrates beyond that area through said recesses when pressure is applied on the impression tray filled with the lining material, then said lining material polymerizes and forms a soft buffer zone between the lower and upper rows of teeth. Since the process can be carried out simply, such a dental guard as that described above can be produced by the sportsman himself.

In the same way the above material may also serve as a molding material which is poured into a prepared impression tray already adapted to the jaw situation of the patient, to obtain a more exact, non-shrinking impression which is true to the model. It is especially advantageous according to the invention that when using an impression tray of acrylate plastic with the mold material also based on acrylate, the use of an adhesive is not required, as is necessary with the commercial molding materials. Thereby in a simple way an improved function impression tray or situation impression for making a denture or partial denture can be made, while producing better-fitting and better-placed prostheses.

I claim:

1. A process for the preparation of dental-technical, dental-medical and medical molding and lining materials, comprising
   mixing a substrate selected from the group consisting of a monomeric and/or polymeric or copolymeric acrylic or methacrylic ester,
   a hardening substance for the substrate, and
   jojoba oil, wherein the jojoba oil is present in an amount of 0.05 to 10% by weight of total material and the substrate is present in an amount of at least about 60% of the total weight of the material.

2. The process according to claim 1, wherein there is further added an accelerator substance for the hardening of the acrylic or methacrylic ester.

3. The process according to claim 1, wherein there is further added a metal soap and/or a silicate.

4. The process according to claim 3, wherein the metal soap is used in an amount of 0.1 to 10% by weight.

5. The process according to claim 3, wherein as metal soap calcium and/or magnesium stearate is used.

6. The process according to claim 3, wherein 1.5 to 5% by weight of alkaline aluminum silicate is used.

7. The process according to claim 1, wherein there is further added a cross-linking agent.

8. The process according to claim 7, wherein as cross-linking agent an olefinic dimethacrylate or a (poly)-ethyleneglycol dimethacrylate is used.

9. A process for the preparation of dental-technical, dental-medical and medical molding and lining materials, comprising the mixing of a two-component system, consisting of (a) a powder system which comprises a polymeric acrylic or methacrylic ester, a metal soap and a hardening substance for the acrylic or methacrylic ester, and (b) a liquid system, consisting of a monomeric acrylic or methacrylic ester and 0.05 to 10% by weight of jojoba oil 10. The process according to claim 1, wherein said molding material is used for the manufacture of dental-technical, dental-medical and medical molds.

11. The process according to claim 1, wherein said molding material is used to form a tooth guard, especially for sportsmen and sportswomen.

12. The process according claim 1, wherein said molding material is used for the preparation of an individually fitted (functional) impression tray.

13. The process according to claim 1, wherein said lining material is used a lining material for dental molds and artificial limbs.

14. The process according to claim 1, wherein said lining material is used in self-medication for the fitting of dentures.

15. An improvement to the process for preparing dental-technical, dental-medical and medical molding and lining materials consisting substantially of a monomeric and/or polymeric or methacrylic ester and a hardening substance, the improvement comprising, mixing 0.05 to 10% by weight of jojoba oil with the monomeric and/or polymeric or copolymeric acrylic or methacrylic ester and hardener before the material polymerizes to become a hard or plastic product.

16. A dental-technical, dental-medical or medical molding or lining material comprising, a substrate selected from the group consisting of a monomeric and/or polymeric or copolymeric acrylic or methacrylic ester, a hardening substance for the respective acrylic of methacrylic ester, and jojoba oil, wherein the substrate and hardening substance are present in an amount equal to about 60% by total weight and the jojoba oil is present in an amount equal to between 0.05 and 10% by total weight.

17. A product as claimed in claim 16, wherein the hardened material has a shore-A-hardness of about 35 at body temperature and a shore-A-hardness of about 70 at room temperature.

18. A product as claimed in claim 16 wherein the substrate includes a monomeric acrylate and the content of unreactive monomeric acrylate in the hardener material is about 1 to 2% at about 10 to 19% refinding (not reactive).

19. A dental-technical, dental-medical or medical molding or lining composition material according to claim 16, in the form of a two-component system, comprising, (a) a powder system which comprises a polymeric acrylic or methacrylic ester, and a hardening substance for the acrylic or methacrylic ester, and (b) a liquid system consisting of a monomeric acrylic or methacrylic ester, jojoba oil and an accelerator, wherein the polymeric and monomeric acrylic or methacrylic ester and the hardening substances are present in an amount equal to about 60% by total weight, and jojoba oil is present in an amount equal to between 0.05 and 10% by total weight.

* * * * *

UNITED STATES PATENT AND TRADEMARK OFFICE
CERTIFICATE OF CORRECTION

PATENT NO. : 4,759,798

DATED : July 26, 1988

INVENTOR(S) : Frauke Hofacker Freifrau von Nostitz

It is certified that error appears in the above-identified patent and that said Letters Patent is hereby corrected as shown below:

On the cover sheet, after "Jan. 14, 1986" and before "[51]" insert --Related U. S. Application Data
Continuation-in-Part of Serial No. 06/659,616, October 11, 1984, abandoned.

Foreign Application Priority Data
Oct. 19, 1983[DE] Fed. Rep. of Germany 3337986
. --

In column 1, line 5, insert --Related Application. This application is a continuation of my application Ser. No. 06/659,616, filed Oct. 11, 1984, now abandoned.--

Signed and Sealed this

Fourteenth Day of March, 1989

Attest:

DONALD J. QUIGG

Attesting Officer

Commissioner of Patents and Trademarks